United States Patent [19]

Ringlien

[11] Patent Number: 5,489,987
[45] Date of Patent: Feb. 6, 1996

[54] CONTAINER SEALING SURFACE INSPECTION

[75] Inventor: James A. Ringlien, Maumee, Ohio

[73] Assignee: Owens-Brockway Glass Container Inc., Toledo, Ohio

[21] Appl. No.: 223,803

[22] Filed: Apr. 7, 1994

[51] Int. Cl.$^6$ ............................................. G01N 21/90
[52] U.S. Cl. ...................... 356/428; 356/240; 250/223 B
[58] Field of Search ........................... 356/426, 428, 356/237, 240, 375, 376; 250/223 B, 560, 563, 572, 561; 209/526; 348/127–129

[56] References Cited

U.S. PATENT DOCUMENTS

| | | |
|---|---|---|
| 3,313,409 | 4/1967 | Johnson . |
| 3,788,741 | 1/1974 | Buechler ................................. 356/371 |
| 3,880,750 | 4/1975 | Butler et al. . |
| 4,198,164 | 4/1980 | Cantor ..................................... 250/561 |
| 4,488,648 | 12/1984 | Claypool ................................. 356/428 |
| 4,491,728 | 1/1985 | Fischer . |
| 4,697,076 | 9/1987 | Yoshida . |
| 4,758,084 | 7/1988 | Tokumi et al. . |
| 4,811,251 | 3/1989 | Minato . |
| 4,900,916 | 2/1990 | Cormack . |
| 4,929,828 | 5/1990 | Claypool . |
| 4,945,228 | 7/1990 | Juvinall et al. . |
| 5,020,908 | 6/1991 | Hermann . |
| 5,200,801 | 4/1993 | Juvinall et al. ......................... 356/428 |
| 5,249,034 | 9/1993 | Minato ................................... 356/240 |

FOREIGN PATENT DOCUMENTS

| | | | |
|---|---|---|---|
| 0065243 | 4/1984 | Japan ..................................... 356/240 |
| 0193009 | 8/1986 | Japan ..................................... 356/428 |
| 0228049 | 9/1988 | Japan ..................................... 356/428 |
| 2112931 | 7/1983 | United Kingdom ................... 356/240 |

Primary Examiner—Hoa Q. Pham

[57] ABSTRACT

Apparatus for inspecting the sealing surfaces of containers that includes a light source positioned to direct a narrow beam of light energy at an acute angle onto the sealing surface of a container as the container is rotated about its central axis. A light sensor is disposed to receive the narrow beam of light energy reflected from the sealing surface, and provides an output signal that varies as a function of position of incidence of the reflected light beam on the sensor. The sensor is coupled to associated electronics for providing information indicative of container height, and a signal for controlling separation of a container from the conveyor system when height of the container, warp or dip of the container sealing surface, or cocked finish at the container exceeds predetermined standards.

15 Claims, 2 Drawing Sheets

CONTAINER SEALING SURFACE INSPECTION

The present invention is directed to inspection of containers, and more particularly to a method and apparatus for measuring variations in level at the sealing surface of a container.

BACKGROUND AND OBJECTS OF THE INVENTION

U.S. Pat. No. 3,313,409 discloses an apparatus for inspecting glass containers in which a starwheel conveys containers in sequence through a series of inspection stations. At one of the inspection stations, selected dimensional parameters of each container are inspected by contacting the container with rollers coupled to sensors, and rotating the container about its central axis so that the sensors provide output signals that vary as a function of variation of the container parameters. Specifically, container height, sealing surface warp and dip, and cocked orientation of the container finish are measured by rollers that engage the container sealing surface as the container rotates. The rollers are coupled to LVDT sensors that provide analog electrical signals indicative of deviations or variations in level (height) at the sealing surface. These signals are fed to appropriate electronics to energize a reject plunger for separating a container from the conveyor line if the measurement signals depart from desired standards and specifications.

Although the inspection system disclosed in the noted patent, assigned to the assignee hereof, has enjoyed substantial commercial success, improvements remain desirable. The rollers in contact with the container sealing surfaces are subject to mechanical wear. The rollers may cause contamination at the sealing surface. The size of the rollers limits the size of containers in connection with which they may be employed, and the size (resolution) of level variations that can be detected. The moving parts require maintenance and repair. It is a general object of the present invention to provide an apparatus and method for inspecting the sealing surfaces of containers for variations in level at the container sealing surface that address and overcome the aforementioned deficiencies in the art.

More specifically, it is an object of the present invention to provide an apparatus and method for measuring level variations in the sealing surfaces of containers that employ electro-optical techniques in which the gauging apparatus does not contact the measurement surface. Another object of the present invention is to provide a method and apparatus of the described character that attains the foregoing objectives, while being economical to implement and reliable over an extended operating lifetime. Yet another and more specific object of the present invention is to provide an electro-optical non-contact method and apparatus for measuring the height of containers at the sealing surfaces, for measuring warp and dip at the sealing surfaces, and for measuring cocked finish of the containers.

SUMMARY OF THE INVENTION

The present invention contemplates a method and apparatus for electro-optically measuring variations in level at the sealing surface of containers by directing a narrow beam of light energy onto the sealing surface from which it is reflected onto a light sensor. The sensor is such as to provide an electrical output that varies as a function of position of incidence of the reflected light beam on the sensor. Thus, any variations in level at the container sealing surface cause a corresponding variation in the point or position at which the reflected light beam impinges upon the sensor, so that the sensor provides an output signal that varies as a direct function of sealing surface level.

Apparatus for inspecting the sealing surface of container finishes in accordance with presently preferred embodiments of the invention includes a light source positioned to direct a narrow beam of light energy onto the sealing surface of a container as the container is rotated about its central axis. A light sensor is disposed to receive the narrow beam of light energy reflected from the sealing surface, and provides an output that varies as a function of position of incidence of the reflected light beam on the sensor. The sensor is coupled to associated electronics for providing information indicative of container height, and a signal for controlling separation of a container from the conveyor system when height of the container, warp or dip of the sealing surface, or cocked finish at the container exceeds predetermined standards.

The light source and sensor in the preferred embodiments of the invention are disposed above the sealing surface of the container, and are oriented with respect to each other and with respect to the container sealing surface such that the beams incident on and reflected from the container sealing surface are in a plane perpendicular to the sealing surface. In one embodiment of the invention, two light source/sensor pairs are disposed on laterally opposed sides of the container, with each sensor providing an output signal that varies as a function of level of the container sealing surface immediately adjacent to the sensor. The two sensors are coupled to electronics for determining variations in level at the sealing surface as a combined function of the two sensor output signals. Thus, dips at the sealing surface and a cocked container finish may be identified and measured as a function of a different between the sensor output signals, while a warped sealing surface may be identified and measured as a function of a sum of the sensor output signals. Height of the container, and variations in height between successive containers conveyed through the inspection station, may be determined as a function of the output of either or both of the sensors.

BRIEF DESCRIPTION OF THE DRAWINGS

The invention, together with additional objects, features and advantages thereof, will be best understood from the following description, the appended claims and the accompanying drawings in which:

DETAILED DESCRIPTION OF PREFERRED EMBODIMENTS

Figure 1:
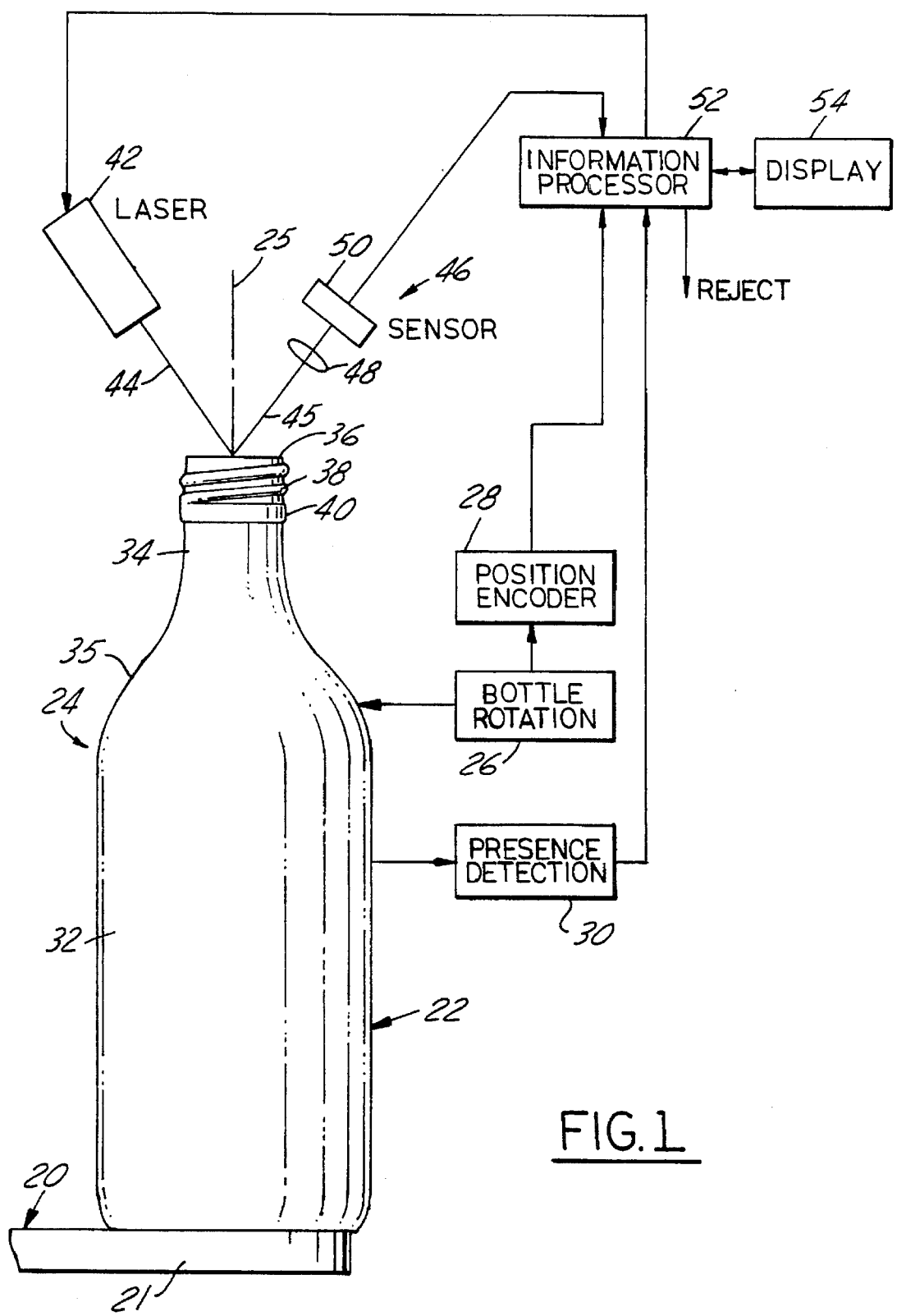
FIG. 1 is a schematic diagram of apparatus for inspecting the sealing surface of containers in accordance with one presently preferred embodiment of the invention.

Referring to FIG. 1, a conveyor 20, typically including a starwheel (not shown) and a slide plate 21, is so disposed and connected to a source of molded containers as to bring successive containers 22 into position at a sealing surface inspection station 24. Such starwheel conveyor container inspection arrangement is disclosed, for example, in above-noted U.S. Pat. No. 3,313,409. A bottle-rotating device 26, such as a drive roller, is positioned to engage each container 22 at station 24 and to rotate the container about its central axis 25 as the container is held in fixed position by the conveyor. An encoder 28 is coupled to the container rotation mechanism to provide signals indicative of increments of container rotation. A detector 30, such as a switch, is positioned to provide a signal indicative of presence of container 22 at station 24.

In the implementation of the present invention illustrated in FIG. 1, container 22 comprises a molded glass bottle having a cylindrical body 32 and a generally cylindrical neck 34 that projects upwardly from the body shoulder 35. The finish portion of the container includes an upper portion of neck 34 that terminates in an axially facing cap sealing surface 36, which is inspected in accordance with the present invention. A helical thread 38 is integrally molded into the outer surface of the finish wall that surrounds the container mouth, or a lip or shoulder 40 is formed on the finish wall outer surface over which a cap skirt may be crimped in the usual manner for affixing the cap to the container. The present invention is directed to a method and apparatus for inspecting height and variations in level of the sealing surface 36 against which the cap seats.

A light source 42, such as a laser or incandescent light source, is positioned above sealing surface 36 of container 22 at station 24, and oriented to direct a narrow collimated beam 44 of light energy downwardly at an acute angle onto sealing surface 36. A camera 46 is also positioned above sealing surface 36 of container 22 at station 24 and oriented to receive the beam 45 reflected from sealing surface 36. Camera 46 includes a focusing lens 48 and a light sensor 50 that provides an electrical output signal indicative not only of incidence of the reflected light energy on the sensor, but also position of incidence on the sensor. An information processor 52 receives signals from detector 30 indicating presence of a container 22 at inspection station 24, and signals from encoder 28 indicative of increments of container rotation. Camera 46 is likewise coupled to information processor 52 for receiving control signals from processor 52, and providing output signals to the information processor indicative of position of incidence of reflected light beam 45 on sensor 50. Light source 42 is likewise controlled by processor 52.

Figure 2A:
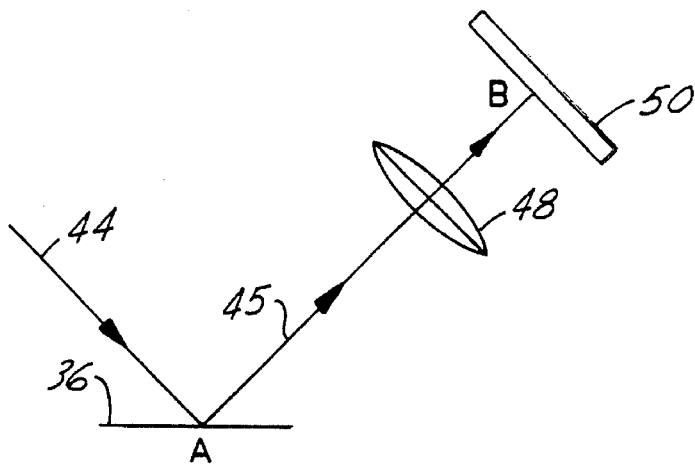
FIGS. 2A and 2B are fragmentary schematic diagrams that illustrate operation of the embodiment illustrated in FIG. 1.
Figure 2B:
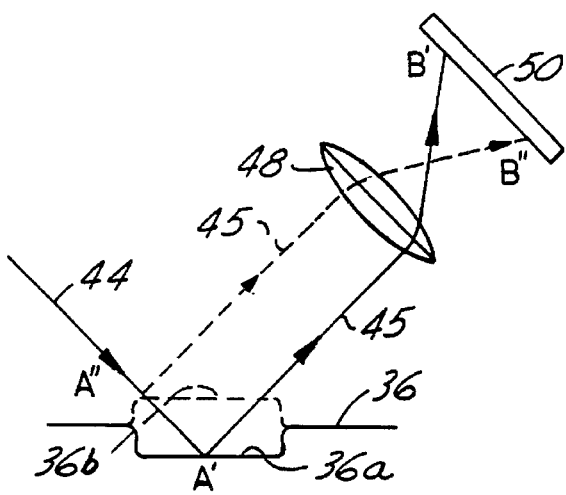

Operation of the embodiment of FIG. 1 is illustrated in FIGS. 2A and 2B. In FIG. 2A, incident beam 44 intersects sealing surface 36 at point A, and is reflected at 45 through lens 48 to impinge upon sensor 50 at point B. In FIG. 2B, beam 44 is incident at point A' within a dip or depression 36a in sealing surface 36. Consequently, reflected light beam 45 is incident on sensor 50 through lens 48 at a different point B'. Since sensor 50 provides an output signal to information processor 52 (FIG. 1) indicative of position of incidence on the sensor, such output signal in FIG. 2B will be different from the signal in FIG. 2A. Consequently, information processor 52 receives an indication of variation of level at the sealing surface at the point of container rotation where depression 36a is encountered, and of a magnitude corresponding to deviation between the nominal point of incidence B in FIG. 2A, and the varied point of incidence B' in FIG. 2B. In the event that depression 36a is of substantial arcuate dimension, the altered sensor output signal in the situation of FIG. 2B will be maintained for a correspondingly greater number of increments of container rotation. On the other hand, if a raised portion 36b is encountered at the sealing surface, the point of incidence B' of reflected light beam 45 on sensor 50 will vary in the opposite direction, providing a corresponding indication to information processor 52.

Thus, the apparatus of FIG. 1 provides signals to information processor 52 not only of changes in level at sealing surface 36 as the container rotates, which may indicate dip, warp or cocked finish, but also of average height of the sealing surface as the container rotates. Such average and/or variations in sealing surface height may be suitably displayed at 54, and are compared within processor 52 to corresponding standards or thresholds. If average sealing surface height is outside of specification, or if warp, dip or cocked sealing surface measurements are outside of acceptable specifications, a reject signal is generated and fed to an appropriate reject mechanism for removing the container from the process line.

Light source 42 and sensor 50 preferably are so disposed above sealing surface 36 of container 22 at station 24 that the incident light beam 44 and reflected light beam 45 are disposed in a plane perpendicular to the nominal plane of the sealing surface. Sensor 50 may comprise a lateral effect diode having a lateral effect axis in the plane of the incident and reflected light beams. Such a lateral reflect diode provides an analog signal to information processor 52 that varies in magnitude as a function of position of incidence of the reflected light beam on the surface of the diode. Alternatively, sensor 50 may comprise a CCD array sensor having a plurality of light sensitive elements disposed in a line in the plane of the incident and reflected light beams. In such an arrangement, the sensor array is scanned by information processor 52, and the position of incidence of the reflected light beam on the sensor array is determined as a function of amplitude of the various element output signals. Such an array sensor preferably would comprise a linear array sensor, or may comprise a matrix array sensor in which one row or column is monitored for sealing surface level measurement purposes.

Figure 3:
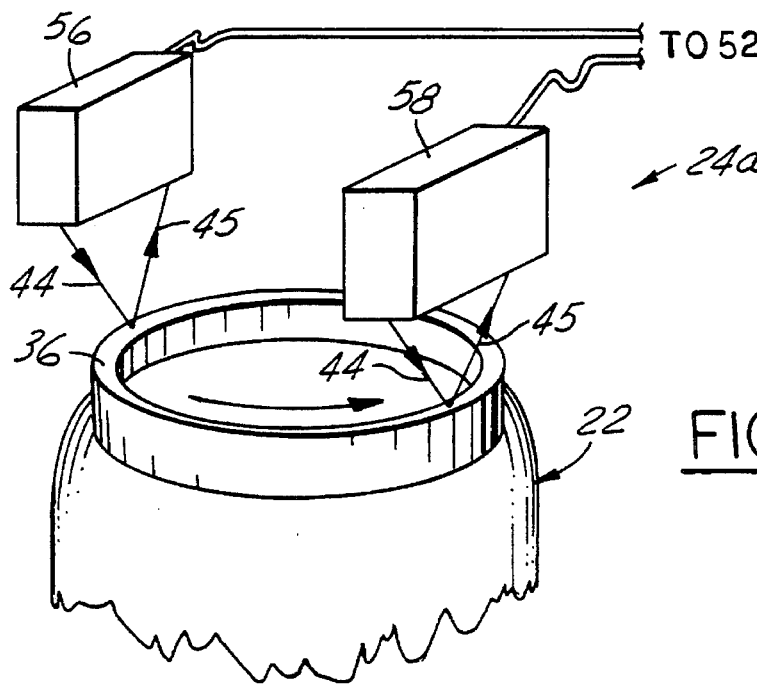
FIG. 3 is a fragmentary schematic diagram of a modified embodiment of the invention.

FIG. 3 illustrates a modified inspection station 24a in which a pair of light source/sensor modules 56,58 are positioned so as to direct respective light beams 44 downwardly onto the sealing surface and receive reflected light beams 45 from the sealing surface on laterally opposed sides of the container mouth. The paired light source/sensor arrangement of FIG. 3 has the specific advantage that the outputs of the respective source/sensor modules 56,58 may be compared in real time for determining height characteristics of container 22 as a combined function of such output signals. That is, cocked finish and dip at sealing surface 36 may be measured as a function of the difference between sealing surface height at the opposite sides of the container mouth, while a warped sealing surface may be identified as a function of the sum of the sensor output signals. Again, the magnitude of the sealing surface height variations may be displayed at 54 (FIG. 1) and compared to appropriate standards or specifications for generation of a reject signal.

I claim:

1. Apparatus for inspecting the finish of a container having a central axis and an open mouth surrounded by an axially facing sealing surface for sealing engagement with a container cap, said apparatus comprising:

means for rotating a container about its central axis, a light source positioned to direct a narrow beam of light energy onto the sealing surface of a container in said rotating means, light sensor means disposed to receive said narrow beam of light energy reflected by the sealing surface, said light sensor means being characterized by providing an electrical output signal that varies as a function of position of incidence of light on said sensor means, said light source and said light sensor means being disposed above the sealing surface of the container in said rotating means and positioned such that said beams incident on and reflected from the sealing surface of the container are in a plane perpendicular to the sealing surface, both said light source and said light sensor means being disposed in said plane, and such that the light beam reflected by the sealing surface of the container onto said light sensor means is incident at a position on said sensor means that varies with level of the sealing surface with respect to said light source and said sensor means, and means for detecting variations in level at the sealing surface of the container as a function of position of incidence of the reflected light beam on said light sensor means as the container rotates.

2. The apparatus set forth in claim 1 wherein said variations-detecting means comprises means for detecting variations in level at the sealing surface as a function of variations in position of incidence of the reflected light beam on said light sensor means as the container rotates.

3. The apparatus set forth in claim 2 comprising first and second light sources and first and second light sensor means disposed in respective pairs on laterally opposed sides of the axis of the container in said rotating means, beams incident on and reflected from the sealing surface being in planes perpendicular to the container sealing surface for each said pair and with each said pair being disposed in its associated plane.

4. The apparatus set forth in claim 3 wherein said variations-detecting means comprises means for detecting variations in level at said sealing means as a combined function of variations in positions of incidence of the reflected light beam on each of said first and second sensor means.

5. The apparatus set forth in claim 4 wherein each of said first and second sensor means provides an electrical signal that varies as a function of position of incidence of the associated reflected beam, and wherein said variations-detecting means comprises means for determining warp at the sealing surface responsive to a sum of said signals.

6. The apparatus set forth in claim 4 wherein each of said first and second sensor means provides an electrical signal that varies as a function of position of incidence of the associated reflected beam, and wherein said variations-detecting means comprise means for determining cock and/or dip at the sealing surface responsive to a difference between said signals.

7. The apparatus set forth in claim 1 wherein said light sensor means comprises a lateral effect diode positioned to have a lateral effect axis in said plane.

8. The apparatus set forth in claim 1 wherein said light sensor means comprises an array of light sensitive elements positioned such that said array is disposed in said plane.

9. The apparatus set forth in claim 1 wherein said light source comprises means for providing said narrow beam in a collimated beam of light energy.

10. The apparatus set forth in claim 9 wherein said light source comprises a laser.

11. Apparatus for inspecting the finish of containers having a central axis and an open mouth surrounded by an axially facing sealing surface for sealing engagement with a container cap, said apparatus comprising:

a light source positioned to direct a beam of light energy onto the sealing surface of a container, light sensor means disposed to receive said beam of light energy reflected by the sealing surface, said light source and said light sensor means being disposed above the sealing surface of the container such that said beams incident on and reflected from the sealing surface of the container are in a plane perpendicular to the sealing surface, both said light source and said light sensor means being disposed in said plane, and means for detecting variations in height of the sealing surface of the container as a function of variations in position of incidence of the reflected light beam on said light sensor means.

12. The apparatus set forth in claim 11 further comprising means for rotating container about its central axis beneath said light source and sensor means.

13. The method of inspecting a container for variations in height at the sealing surface of the container comprising the steps of:

(a) rotating the container about its axis, (b) directing a beam of light energy at an acute angle onto the sealing surface of the container as it rotates such that the beam is incident upon and reflected from the sealing surface in a plane perpendicular to the sealing surface, (c) positioning a light sensor in said plane to receive the light beam reflected from the sealing surface such that the light beam reflected by the sealing surface of the container onto the light sensor is incident at a position on said sensor that varies with level of the sealing surface with respect to said sensor, and (d) detecting variations in height at the sealing surface of the container as a function of variations in position of incidence of the reflected light beam on said sensor as the container rotates.

14. The method set forth in claim 13 comprising the additional steps of:

(e) directing a second beam of light energy at an acute angle onto the sealing surface of the container as it rotates such that the beam is incident upon and reflected from the sealing surface in a second plane perpendicular to the sealing surface, (f) positioning a second light sensor in said second plane to receive the second light beam reflected from the sealing surface, and (g) detecting warp, dip and/or cock at the sealing surface of the container as a combined function of variations in position of incidence of the reflected light beams on said sensors as the container rotates.

15. The method set forth in claim 14 wherein said planes are on laterally opposed sides of the container axis.

* * * * *